United States Patent [19]

Pokora et al.

[11] Patent Number: 5,491,085
[45] Date of Patent: Feb. 13, 1996

[54] METHOD OF RECOVERING PEROXIDASE FROM SEED HULLS USING A FREEZE-THAW TECHNIQUE

[75] Inventors: Alexander R. Pokora, Pickerington; Mark A. Johnson, Chillicothe, both of Ohio

[73] Assignee: Enzymol International, Inc., Columbus, Ohio

[21] Appl. No.: 699,905

[22] Filed: May 14, 1991

[51] Int. Cl.$^6$ ............................... C12N 9/08; C12N 9/06; C12N 9/04

[52] U.S. Cl. ..................... 435/192; 435/189; 435/190; 435/814; 435/816

[58] Field of Search .................................. 435/190, 192, 435/189, 814, 816

[56] References Cited

U.S. PATENT DOCUMENTS

| | | |
|---|---|---|
| 3,947,324 | 3/1976 | Lakshminarayanan ............... 195/66 R |
| 4,228,240 | 10/1980 | Dawson et al. ........................ 435/188 |
| 4,698,306 | 10/1987 | Noda et al. ............................ 435/192 |

FOREIGN PATENT DOCUMENTS

| | | |
|---|---|---|
| 2072874 | 9/1988 | Japan . |
| 1108102 | 8/1984 | U.S.S.R. ............................... 435/192 |

OTHER PUBLICATIONS

Albara et al. *J. of Biochem.* 90. pp. 489–496. (1981).

*Primary Examiner*—Marian C. Knode
*Assistant Examiner*—L. Blaine Lankford
*Attorney, Agent, or Firm*—Thompson, Hine and Flory

[57] ABSTRACT

Peroxidase can be recovered from seed hulls in an improved method using a freeze-thaw technique. First, the seed hulls are comminuted, placed into water and homogenized. Next, the homogenate is frozen then thawed. The enzyme is then recovered from the aqueous solution by conventional means. Soybean or rice seed hulls can be used in this process.

9 Claims, No Drawings

METHOD OF RECOVERING PEROXIDASE FROM SEED HULLS USING A FREEZE-THAW TECHNIQUE

BACKGROUND OF THE INVENTION

In U.S. application Ser. No. 599,584 filed Oct. 18, 1990, now U.S. Pat. No. 5,147,793, a process for polymerizing certain phenols by oxidative coupling in the presence of soybean peroxidase and other plant peroxidases is disclosed together with a number of other applications in which these peroxidases may be used.

In view of the enhanced value of soybean and other peroxidases fostered at least in part by the teachings in the aforementioned application, there is a need for a more efficient method for recovering this enzyme.

SUMMARY OF THE INVENTION

The present invention relates to an improved method for recovering peroxidase enzyme from plant extracts and more particularly from the hulls of soybeans and other legumes wherein a homogenate of the hulls is frozen to accelerate sedimentation of the particles forming the homogenate and separation of the extract.

The invention resides in a method which comprises the steps of:

preparing a homogenate of a peroxidase-containing plant part in water, freezing said homogenate, thawing said frozen homogenate, and separating the particles from said homogenate to obtain an extract containing said peroxidase.

DETAILED DESCRIPTION OF THE INVENTION

The invention will be specifically described with reference to recovering soybean peroxidase from soybean hulls, however, those skilled in the art will understand that peroxidases can also be obtained from the hulls of other legumes such as peas and beans (e.g., guar, garbanzo, runner, etc.), from horseradish roots and from other plants such as rice hulls in accordance with the invention.

As a first step in the process, a homogenate of the portion of the plant containing peroxidase (e.g., the hull or root) in water is prepared. This can be accomplished by milling, blending or grinding, but the most efficient technique uses an emulsifier. The speed and time of emulsification will vary as a function of concentration, emulsifier design and other factors. Generally, emulsification is continued until a particle size of about 30 mesh is achieved. One emulsifier useful in the present invention is a Ross Model 100L emulsifier. Using this equipment at its maximum speed (13,000 rpm) about 30 seconds is required to homogenize the hulls. In commercial processes commercial size continuous or batch emulsifiers may be used. (The term "homogenize" and any derivations thereof are loosely used in that following homogenization there may be some settling of larger particles which would not be observed in a true homogenate).

The concentration of hulls to water used in preparing the homogenate is typically about 10% but may range from about 1 to 30% by weight.

After homogenizing the hulls, the homogenate is preferably filtered to remove the larger particles. This can be done using cheese cloth or a 30 mesh screen.

The filtered homogenate may be frozen directly. For some of the experimental work described herein, the homogenate is diluted to 10%–80% of its original concentration. This was done to enable more accurate measurement of the sedimentation rates and is not a necessary aspect of the invention.

To freeze the homogenate, temperatures on the order of $-20°$ to $-5°$ C. are required. The temperature will vary with concentration, more concentrated homogenates requiring lower temperatures than less concentrated ones. It is preferred to freeze the homogenate to a hard solid. Experiments have been done in which the homogenate is frozen to a slush with less efficiency.

To thaw the frozen homogenate, the homogenate may be heated or simply allowed to sit at room temperature. In heating, however, because peroxidase is a protein care must be taken not to heat locally to temperatures which denature it.

Upon thawing the homogenate, the particles readily settle. The particles can then be removed by conventional techniques including filtration (paper, bag, etc.), centrifugation, decantation, etc. Following this procedure, the extract may be used as is, lyophilized or the enzyme may be recovered by ultrafiltration, ion exchange, or the like.

Various modifications can be made in the process to enhance recovery of the enzyme. As indicated in U.S. application Ser. No. 599,584, yields improve when the hulls are pretreated in toluene. Certain agents such polyethyleneimine, polyvinyl alcohol, polyvinyl pyrrolidone, calcium chloride, and ammonium sulfate, which behave as or somewhat like flocculating agents can be used to enhance separation.

It is reiterated that the process of the invention, broadly stated resides in clarification of a plant extract containing a peroxidase. In addition to hulls, other plant parts containing peroxidase can be homogenized to produce an extract which can be clarified in accordance with this invention.

The invention is illustrated in more detail by the following examples:

Example 1

Soybean seed hulls were obtained in a dry state from a soybean processor. 50 g whole hulls were homogenized with a Ross Model 100L emulsifier (13,000 rpm) for 30 seconds in 500 ml tap water. This process emulsified the sample and extracted the soluble enzyme peroxidase. The yield of enzyme was 265 units/gram dry hull weight based on a pyrogallol assay (Simga Chemical Company, Peroxidase Bulletin).

The soybean seed hull extract was diluted into several fractions at different percentages of the starting concentration in water: 10%, 20%, 40%, 60% and 80%. A portion of each dilution was placed in the freezer ($-20°$ C.), another portion was stored in the refrigerator ($5°$ C.). After 2 hours, the samples were transferred to room temperature and their spectrophotometric, enzymatic and chemical composition were determined. The samples stored in the freezer were completely frozen and thawed prior to analysis at room temperature ($23°$ C.).

A spectrophotometric analysis of the absorbance against water, from 1100 nm to 200 nm, was done on the samples after treatment. Higher absorbance was observed at all wavelengths with the refrigerated extract compared to the freeze-thaw treated extract.

A wavelength in the visible region was chosen to measure the rate of particle settling (700 nm) based on absorbance spectra. The rate of particle settling was compared using extract diluted to 10% of the original concentration. Actual absorbance values were recorded every 1000 seconds and plotted. The tests were done with a circulating water bath set at 23° C. attached to the jacket of the spectrophotometer cells. The results showed that absorbance drops to a level about ½ of the refrigerator stored extract with the freeze-thaw treatment (at 10% of the original extract concentration) in 90 minutes. This result shows a substantially lower particle concentration and increased rate of particle settling in the thawed sample even at the greatest sample dilution tested.

The difference in particle concentration between treated and control extracts was measured simultaneously by placing the freeze-thaw treated sample in the reference cell of a dual beam spectrophotometer and the control refrigerator-stored extract in the test cell. The percent transmittance was measured as the difference of these samples at 5 wavelengths for each dilution. The results are shown in Table 1.

TABLE 1

Percent Transmittance Comparison

| Percent of Original Concentration | Wavelengths (nm) | | | | |
|---|---|---|---|---|---|
| | 1100 | 900 | 700 | 500 | 400 |
| 10 | 85 | 77 | 63 | 47 | 37 |
| 20 | 42 | 30 | 18 | 9.8 | 7.8 |
| 40 | 10 | 5 | 3 | 1.8 | 2.0 |
| 60 | 2.6 | 1.5 | 0.9 | 0.8 | 1.7 |
| 80 | 1.2 | 0.8 | 0.5 | 0.4 | 0.8 |
| 100 | 0.7 | 0.5 | 0.3 | 0.3 | 0.3 |

The results in Table 1 show that for all concentrations tested and at a wide range of wavelengths from near IR to near UV, the refrigerator-stored sample transmitted from 15%–99.7% less light than the freeze-thaw treated extracts, confirming the substantially lower particulate concentration in the treated samples. Absorbance was also measured at these wavelengths and the same trend was confirmed.

Each of the treated and control samples were analyzed for protein, carbohydrate and peroxidase activity by standard methods after 24 hours of settling. This was done to confirm the enhancement of peroxidase quality due to the freeze-thaw treatment. These results are summarized in Table 2.

TABLE 2

Compositions of Soybean Hull Extracts After 24 Hours Settling Time

| Percent Concentration F = Freeze-Thaw R = Refrigerated | Peroxidase Units/ml | Protein mg/ml | Carbohydrate mg/ml |
|---|---|---|---|
| 10F | 1.16 | .079 | .633 |
| 10-R | 1.43 | .196 | 1.154 |
| 20-F | 3.13 | .094 | 1.976 |
| 20-R | 3.12 | .455 | 2.11 |
| 40-F | 7.38 | .164 | 3.33 |
| 40-R | 8.56 | .648 | 3.71 |
| 60-F | 11.76 | .136 | 3.57 |
| 60-R | 15.10 | .674 | 5.80 |
| 80-F | 17.97 | .169 | 4.83 |
| 80-R | 20.93 | 2.238 | 8.57 |
| 100-F | 23.0 | .292 | 5.70 |
| 100-R | 26.5 | 2.557 | 8.97 |

Results from Table 2 show that the freeze-thaw cycle leads to minimal, if any, loss of peroxidase activity, a slight decrease in total carbohydrate, and a substantial loss of total protein. Results in Table 2 follow the trends shown in Table 1. The effect of the freeze-thaw treatment is greater at higher extraction concentrations.

The value freeze-thaw treatment can be shown by the ratio of peroxidase activity to total protein (specific activity). A highly enriched peroxidase has a high specific activity, a measure of enzyme purity. The specific activity was calculated from Table 2 for each sample and the fold purification was determined as the ratio of specific activities of treated to untreated samples. The results are shown in Table 3.

TABLE 3

Purification of Soybean Peroxidase

| Percent of Original Concentration | Specific Activity | Fold Purification |
|---|---|---|
| 10-F | 14.7 | 2.0 |
| 10-R | 7.3 | |
| 20-F | 33.3 | 4.8 |
| 20-R | 6.9 | |
| 40-F | 45 | 3.4 |
| 40-R | 13.2 | |
| 60-F | 86.5 | 8.2 |
| 60-R | 10.6 | |
| 80-F | 106 | 11.4 |
| 80-R | 9.4 | |
| 100-F | 78.8 | 7.6 |
| 100-R | 10.3 | |

The results from Table 3 show that the enrichment in peroxidase increases from 2-fold to 11-fold with increasing extract concentration.

Analysis of treated samples compared with controls shows that particulate contamination can be removed quickly (2 hours) by a freeze-thaw cycle and settling by the force of gravity. The treatment results in a highly enriched peroxidase which is suitable for processing by ultrafiltration and contributes little interference or contamination in phenolic polymerization reactions.

Example 2

A soybean hull extract was prepared as described in Example 1 This sample was a concentrated form of the extract prepared without further dilution. Aliquots (3 ml each) were cooled to various temperatures according to Table 4 to determine the effect of freezing on separation. After incubation, the samples were equilibrated at room temperature (23 deg C.) for 1 hour, centrifuged at 1,500×g for 8 minutes and the percent transmittance at 700 nm was determined in a Shimadzu UV-visible double beam recording spectrophotometer against water at 23 degrees C.

TABLE 4.

| Temperature Deg C. | Time of Preincubation Hours | Sample Condition | % Transmittance At Room Temp. |
|---|---|---|---|
| −15 | 2 | Solid | 89 |
| −5 | 0.16 | Slush | 14 |
| 0 | 4 | Liquid | 0.8 |
| 5 | 4 | Liquid | 0.9 |

The results in Table 4 show that removal of particles, indicated by % transmittance is more efficient when the sample was completely frozen. The concentrated state freezes at temperatures lower than zero degrees C. because of a high level of dissolved impurities. A more dilute sample freezes readily.

Example 3

Settling of particles in thawed samples of a diluted extract was studied using the change in absorbance at a visible wavelength of 700 nm. At this value, absorbance of light is primarily due to particle concentration, according to the Beers-Lambert Law. Absorbance at 700 nm is directly related to particle concentration. The experiment was performed as follows:

Soybean extract was diluted 5-fold with water at room temperature. Diluted extract (3 ml) was placed in a spectrophotometer cuvette and absorbance against water was determined at 700 nm over a course of time and temperature increase. A jacketed cuvette holder was used, attached to a Haake constant temperature circulating water bath (1 gal) capable of controlling temperature within the range of experimental design (−15 to +25 degrees C.). The sample and reference cuvettes were cooled to a constant temperature while monitoring the absorbance at 700 nm for 10 minutes, then the temperature was increased at a steady 2.5 degrees per minute until +25 degrees C. was reached. Absorbance did not change significantly during the initial 10 minute constant temperature equilibration. The decline in absorbance, indicating a lower particle concentration due to settling, was recorded every 100 seconds during the temperature increase to 25 degrees.

Results indicated that pretreatment between −15 and −5 degrees C. is adequate to get precipitation of particles, as long as the sample freezes. Treatment at 0 degrees and above is inadequate for efficient particle separation at the concentration tested.

Having described the invention in detail and by reference to preferred embodiments thereof, it will be apparent that modifications and variations are possible without departing from the scope of the invention defined in the appended claims.

What is claimed is:

1. A method for recovering peroxidase as a solution in water comprising:

preparing a homogenate of seed hulls containing peroxidase in water, freezing said homogenate, thawing said frozen homogenate, and separating the particles from said homogenate to obtain a solution of said peroxidase in said water.

2. The method of claim 1 wherein said homogenate is prepared by emulsifying said hulls in water at a concentration of about 1 to 30% by weight.

3. The method of claim 2 wherein said homogenate is filtered prior to said step of freezing.

4. The method of claim 3 wherein said homogenate is frozen to a completely solid mass.

5. The method of claim 4 wherein said hulls are soybean hulls.

6. The method of claim 2 wherein said homogenate has a particle size of about 30 mesh.

7. The method of claim 3 wherein said homogenate is frozen to a slush.

8. A method for recovering peroxidase as a solution in water from a plant part containing peroxidase comprising:

preparing a homogenate of said plant part in water, freezing said homogenate, thawing said frozen homogenate, and separating the particles from said homogenate to obtain a solution of peroxidase in water.

9. The method of claim 8 wherein said plant part is horseradish root.

* * * * *

UNITED STATES PATENT AND TRADEMARK OFFICE
CERTIFICATE OF CORRECTION

PATENT NO.  : 5,491,085

DATED       : February 13, 1996

INVENTOR(S) : Alexander R. Pokora et al.

It is certified that error appears in the above-indentified patent and that said Letters Patent is hereby corrected as shown below:

On the title page, item [54] and column 1, line 2, change "METHOD OF" to --METHOD FOR--.

Claim 1, Col. 6, line 5, after "water" insert --from seed hulls--.

Signed and Sealed this

Eleventh Day of June, 1996

Attest:

BRUCE LEHMAN

*Attesting Officer*          *Commissioner of Patents and Trademarks*